(12) United States Patent
Raiche et al.

(10) Patent No.: US 7,495,052 B2
(45) Date of Patent: Feb. 24, 2009

(54) METHOD FOR THE PRODUCTION OF POLYMERIZED NANOPARTICLES AND MICROPARTICLES BY TERNARY AGENT CONCENTRATION AND TEMPERATURE ALTERATION INDUCED IMMISCIBILITY

(75) Inventors: Adrian T. Raiche, Fairport, NY (US); Joseph C. Salamone, Fairport, NY (US); Jeffrey Linhardt, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 864 days.

(21) Appl. No.: 10/941,163

(22) Filed: Sep. 15, 2004

(65) Prior Publication Data
US 2006/0057222 A1 Mar. 16, 2006

(51) Int. Cl.
*C08K 3/20* (2006.01)
(52) U.S. Cl. .................. 524/457; 524/458; 524/725; 524/765
(58) Field of Classification Search .......... 524/457, 524/458, 725, 765
See application file for complete search history.

(56) References Cited

U.S. PATENT DOCUMENTS

| | | | |
|---|---|---|---|
| 5,118,528 A | 6/1992 | Fessi et al. | |
| 5,316,768 A | 5/1994 | Hughes et al. | 424/433 |
| 5,542,935 A | 8/1996 | Unger et al. | 604/190 |
| 5,660,851 A | 8/1997 | Domb | 424/427 |
| 6,051,576 A | 4/2000 | Ashton et al. | 514/255 |
| 6,143,037 A | 11/2000 | Goldstein et al. | 623/66 |
| 6,143,276 A | 11/2000 | Unger | 424/9.3 |
| 6,248,724 B1 | 6/2001 | Moore et al. | 514/44 |
| 6,406,745 B1 | 6/2002 | Talton | 427/213 |
| 6,443,898 B1 | 9/2002 | Unger et al. | 600/458 |
| 6,455,250 B1 | 9/2002 | Aguilera et al. | 435/6 |
| 6,537,579 B1 | 3/2003 | Desai et al. | 424/489 |
| 6,579,519 B2 | 6/2003 | Maitra et al. | 424/78.04 |
| 6,608,101 B1 | 8/2003 | Ni et al. | 514/443 |
| 6,632,934 B1 | 10/2003 | Moreadith et al. | 536/23.1 |
| 6,669,959 B1 | 12/2003 | Adjei et al. | 424/489 |
| 6,686,393 B1 | 2/2004 | Hughes et al. | 514/561 |
| 6,696,084 B2 | 2/2004 | Pace et al. | 424/451 |
| 6,709,622 B2 | 3/2004 | Billiet et al. | 264/432 |
| 6,720,007 B2 | 4/2004 | Walt et al. | 424/489 |
| 2001/0042932 A1 | 11/2001 | Mathiowitz et al. | |
| 2003/0138557 A1 | 7/2003 | Allison | |

FOREIGN PATENT DOCUMENTS

EP 1652517 A1 5/2006

*Primary Examiner*—Edward J Cain
(74) *Attorney, Agent, or Firm*—Toan P. Vo

(57) ABSTRACT

Polymerized drug delivery devices are described. Additionally, methods are described for producing and for using polymerized particles for use as drug delivery devices.

20 Claims, No Drawings

METHOD FOR THE PRODUCTION OF POLYMERIZED NANOPARTICLES AND MICROPARTICLES BY TERNARY AGENT CONCENTRATION AND TEMPERATURE ALTERATION INDUCED IMMISCIBILITY

FIELD OF THE INVENTION

The present invention relates to a method for producing polymerized or crosslinked nanoparticle- and microparticle-sized spherical particles potentially consisting of or including one or more active agents. More particularly, the present invention is a method for producing nanoparticle- and microparticle-sized spherical particles useful as pure entities and as drug delivery agents, and a method for incorporating one or more active therapeutic agents uniformly or non-uniformly within the spherical particles.

BACKGROUND OF THE INVENTION

Medication of the eyes is done commonly for two purposes—to treat the exterior of the eyes for infections such as conjunctivitis, blepharitis and keratitis sicca, and to treat the interior of eyes, i.e., intraocular treatment, for diseases such as glaucoma or uveitis. Most ocular diseases are treated through topical applications of solutions administered as eye drops. One major problem encountered with topical delivery of ophthalmic drugs is the rapid and extensive loss of drug through drainage and high tear fluid turn over. After instillation of an eye-drop in an eye, typically less than 2 to 3 percent of the applied drug penetrates the cornea. A major fraction of such instilled doses are often absorbed systematically via the conjunctiva and nasolacrimal duct. Another limitation encountered with topical delivery is a relatively impermeable corneal barrier that limits ocular absorption.

Due to inherent problems associated with the delivery of conventional ophthalmic therapeutic agents, significant effort has been directed to the development of new delivery systems such as hydrogels, nanoparticles, microparticles, liposomes and collagen shields. Ocular drug delivery is an approach to controlling and ultimately optimizing the delivery of therapeutic agents or drugs to their target tissues within the eye. Most formulation efforts to date aim to maximize ocular therapeutic agent or drug absorption by prolonging residence time on the cornea and in the conjunctival sac. Methods of prolonging such residence time include slowing the therapeutic agent or drug release rate from the delivery system and minimizing precorneal drug loss.

Many methods for the production of non-polymerized microspherical- and nanospherical-sized particles and methods for incorporating therapeutically active agents evenly throughout and as central cores within the microspherical and nanospherical particles for ophthalmic delivery are known. One method for producing particles in the microspherical-size range uses monomer directly or a solvent as a polymer or matrix sphere-forming agent that is immiscible with a bulk non-solvent. A surfactant may also be used to stabilize the emulsion formed from the immiscibility of the monomer or solvent and bulk non-solvent. Immiscibility of the monomer or solvent and non-solvent induces a lower limit on the size of the particles that form. In a static state, the monomer or solvent and non-solvent separate into two layers with the less dense layer over the denser layer. Dispersion or emulsification of the two immiscible layers results from some form of agitation, such as ultrasonic waves, mechanical mixing or stirring, and/or vortexing. Polymerization or crosslinking reaction is effected by the addition of energy such as heat or light to form the particle. Where solvents are used to mediate particle formation, hardened microparticle spheres are then formed by removal of the solvent by evaporation. The very small amount of solvent dissolved in the non-solvent is evaporated, and solvent contained in the stable emulsion droplets dissolves into the non-solvent to again saturate the solution.

The addition of dispersive energy competes with the immiscibility of the two solvents or non-solvent and monomer, acting to reduce the solvent phase droplet dimension, causing the latter to reform larger droplets. The resulting size of the microspherical particles is the balance of the two tendencies. Increasing the amount of a particular type of dispersive energy will balance the tendencies at a smaller final microspherical particle size. However, addition of dispersive energy becomes exponentially less effective, while the tendency for smaller droplets to aggregate into larger ones increases exponentially as size decreases. Using an immiscible solvent/non-solvent system, it is difficult to obtain particles smaller than 500 nm in size. Because the energy spectrum used to disperse the solvent in the non-solvent is usually broad, a continuous range of size equilibriums exist. This creates a range of final particle sizes. Additionally, based on available means to introduce dispersive energy into the emulsion, the more energy that is added in an attempt to make smaller final particles, the greater the energy spectrum. Particle size distributions increase substantially as mean particle size decreases.

To produce particles smaller than 500 nm, the constraint of the tendency for droplets to aggregate is removed by using a solvent for the monomer, polymer, or matrix that is miscible with a non-solvent bulk phase. Because the formation process is not dependent on the initial formation of stable emulsion droplets, surfactants can be eliminated. Variations of this method have been named nanoprecipitation and spontaneous emulsification solvent diffusion (SESD), which includes of all such methods characterized by a miscible solvent/non-solvent system used with or without surfactant. Additionally, prior art also describes using a second solvent that serves as a solvent for the polymer or matrix and a second agent, but is immiscible with the non-solvent. A solution is made of the first two solvents and subsequently added to the non-solvent. This represents a combined approach where the first solvent, miscible in the bulk non-solvent, immediately diffuses out of the spontaneous emulsion, but the second solvent, immiscible in the bulk non-solvent, is removed more slowly.

The advantage of methods involving some portion of a miscible solvent is the reduced capacity of aggregation, thus producing narrow size distributions of particles having a mean size less than 500 nm. The limitation with nanoprecipitation lies in the formation of a narrow size distribution of particles with a mean size from 500 nm to 1 mm in diameter. The terms "nanoprecipitation" and "spontaneous emulsification" highlight the functional aspects of these methods. It is the polymer or matrix that emulsifies in the solvent/non-solvent solution, that then precipitates on the addition of the polymer- or matrix-containing solvent to the non-solvent. The precipitation is caused by the insolubility of the polymer or matrix in the solvent/non-solvent system. Emulsification refers to the ability of the solvent to act as a plasticizer in allowing the polymer or matrix to behave as a fluid. Such enables reorganization on the same time scale as that of solvent diffusion. Hardened particles smaller than 500 nm are thus formed.

The limitation in nanoprecipitation/SESD methods arises from the practically instantaneous rate of nanoparticle formation. This places extreme requirements on the rate of the polymeriziation or crosslinking reaction.

A third method for formation of microparticles and nanoparticles involves using a monomer, monomer solution, or functionalized polymer or matrix solvent solution. Microspherical or nanospherical particles are made by initiating the reaction of monomer or functionalized polymer or matrix. The increase in molecular originates insolubility of the resulting polymer or crosslinked polymer or matrix, causing particle precipitation. The limitation of this particular method is that the solvent must be a solvent for unreacted precursor, not reacted material. Such limits the selection of polymers from which one may choose as well as ultimate molecular weight or particle size. The advantage of this method is the seamless transition of a narrow distribution of particle sizes from 1 nm up to 10 µm achieved by "growing" spheres.

Clearly, it is preferable that any ocular drug delivery system does not impair vision and reliably delivers the desired amount of therapeutic agent or drug to the targeted tissues within the eye. Therefore, the materials used to produce oclular drug delivery systems should be biocompatible, non-irritating to ocular tissues and not cause blurring or visual impairment upon use thereof.

SUMMARY OF THE INVENTION

The present invention relates to polymerized drug delivery devices, methods for the production of such drug delivery devices and uses for the drug delivery devices in the ophthalmic field. Polymerization of monomers or crosslinking of macromonomers allows for formation of particles that are insoluble in a bulk fluid regardless of solubility of starting material. Additionally, the presence of crosslinks can control release rate directly by altering diffusivity of therapeutic agent through the particle material or indirectly by increasing particle stability. Polymerized drug delivery devices of the present invention in the form of polymeric particles are useful for the delivery of therapeutically effective amounts of one or more therapeutically active agents such as but not limited to ophthalmic therapeutic agents. Polymeric spherical particles of the present invention are particularly useful in the field of ophthalmology due to the fact that the size of the subject particles may be controlled so as to not alter or only temporarily minimally alter visual acuity. Unaltered visual acuity during use leads to higher user compliance and greater universal appeal than traditional therapeutic treatments, which may temporarily blur or obscure vision.

The subject polymeric spherical particles are effective in the delivery of therapeutically effective amounts of one or more therapeutically active agents. Additionally, the subject polymeric spherical particles are biocompatible and cause little or no tissue irritation.

Accordingly, it is an object of the present invention to provide a method for the production of polymerized particles useful as drug delivery agents.

Another object of the present invention is to provide a method for the production of drug delivery agents useful in ophthalmic applications.

Another object of the present invention is to provide a method for the production of polymeric spherical particles containing a therapeutically effective amount of a therapeutically active agent.

Another object of the present invention is to provide a method for the production of biocompatible particles for ophthalmic drug delivery.

Another object of the present invention is to provide a method for the production of biocompatible particles for ophthalmic drug delivery without or with minimal eye irritation.

Still another object of the present invention is to provide a method for the production of polymeric spherical particles useful in ophthalmic applications without or with minimal visual acuity alteration.

These and other objectives and advantages of the present invention, some of which are specifically described and others that are not, will become apparent from the detailed description and claims that follow.

DETAILED DESCRIPTION OF THE INVENTION

The present invention relates to polymeric particles suitable for use as drug delivery devices which may be controlled to be smaller than the wavelength of light, ranging in size from about 0.10 nm to about 1 mm, preferably about 0.10 nm to less than about 400 nm, more preferably from about 0.25 nm to about 375 nm, and most preferably ranging in size from about 0.50 nm to about 350 nm. The subject drug delivery devices are useful for the delivery of drugs in a targeted fashion through delivery directly into the eye, such as for example by injection, without alteration of vision. The desired drug may be so delivered to the anterior chamber of the eye or the posterior chamber of the eye including for example the vitreous, intraretinal space, subretinal space, intrachoroidal space and the suprachoroidal space. The subject drug delivery device is useful for the control or reversal of diseases of the posterior of the eye including for example but not limited to glaucoma, uveitis, age-related macular degeneration, retinitis pigmentosa, diabetic macular edema, nonproliferative and proliferative diabetic retinopathy, idiopathic premacular fibrosis, Terson syndrome, VX2 intraocular tumors and enophthalmitis.

Methods for producing polymeric particles in accordance with the present invention can be accomplished through either one of two routes. One route is a process in which one or more therapeutically active agents are not soluble in one or more solvents or solvent system in which one or more therapeutically inactive agents are soluble. Examples of such a process include for example but are not limited to fluidized bed coating, precipitation of therapeutically inactive coatings from solution, polymerization of therapeutically inactive coatings and spraying or cospraying of therapeutically active and inactive agents as described in more detail in the examples below. Another route is a process in which both one or more therapeutically active agents and one or more therapeutically inactive agents are soluble in one or more solvents or solvent system. Examples of such a process include for example but are not limited to nanoprecipitation, spray drying, emulsification, and all forms of solvent removal into liquid or gas phase or monomer polymerization as described in more detail in the examples below.

Critical components to the preferred method of the present invention include: 1) a solvent miscible or soluble in a non-solvent; 2) a solvent/non-solvent system in which the polymer or matrix is soluble; 3) a ternary agent soluble in the non-solvent and the solvent/non-solvent system but not soluble in the solvent; 4) a solvent having temperature dependent solubility in a solution of the non-solvent and ternary agent; and 5) a surfactant soluble in the non-solvent and solvent/non-solvent system but not soluble in the solvent. Such polymeric particles made in accordance with the present invention with therapeutically effective amounts of therapeutically active agents incorporated therein are produced using an agent solvent that: 1) is miscible or soluble in a non-solvent; 2) is not a good solvent for a ternary agent that is soluble in the non-solvent; 3) has temperature dependent solubility in a solution of the non-solvent and ternary agent; 4) is not a solvent for a surfactant that is soluble in the non-solvent; and 5) is part of a solvent/non-solvent system that is a solvent for one or more therapeutically active agents to be incorporated. The solvent for the therapeutically active agent(s) or "agent solvent" may be identical to or different than the solvent for the polymer or matrix. The solvent for the therapeutically active agent or agent solvent may or may not be a solvent for the polymer or matrix or a combination thereof.

One or more solvents may be used in accordance with the present invention. Suitable solvents for use in the method of the present invention include solvents miscible or highly soluble in a selected non-solvent such as for example but not limited to acetone, acetonitrile, ethanol, isopropyl alcohol, dimethyl sulfoxide, dimethyl formamide, tetrahydrofuran and dioxane. Preferred solvents include acetone and acetonitrile because their relatively strong solvent nature allows for particle formation of many materials. The volume of one or more solvents used in the present method is typically in the range of about 5 percent to about 50 percent.

One or more non-solvents may be used in accordance with the present invention. Suitable non-solvents for use in the method of the present invention include for example but are not limited to water, ethanol and methanol. The preferred non-solvent is water because of the ability to use secondary factors such as for example pH to further control particle formation processes. The volume of one or more non-solvents used in the present method is typically in the range of about 50 percent to about 75 percent of the solvent/non-solvent system.

Solvent/non-solvent systems of the present invention may include one or more solvents and/or one or more non-solvents. Suitable solvent/non-solvent systems for use in the method of the present invention include for example but are not limited to acetone/water and acetonitrile/water. The preferred solvent and non-solvent system is acetone/water because phase separation can be controlled through a wide range of ternary agent concentrations. The volume of solvent/non-solvent system used in the present method is typically in the range of about 10 mL to about 100 L.

One or more ternary agents may be used in accordance with the present invention. Suitable ternary agents for use in the method of the present invention include for example but are not limited to ammonium azide, ammonium bisulfite, barium acetate hydrate, barium hypophosphate, cadmium chloride, calcium acetate dihydrate, calcium chromate, calcium ethyl methyl acetate, cobalt perchlorate, iron perchlorate hexahydrate, lead chlorate hydrate, lithium hydroxide monohydrate, lithium sulfate, lithium sulfite monohydrate, potassium carbonate, potassium chloride, potassium phosphate, sodium selenate, sodium phosphate, sodium stannate (hydroxo), strontium acetate and yttrium chloride. Preferred ternary agents include sodium chloride and sodium bromide because of their strong interactions with non-solvents such as for example water, leading to solvent phase separation. The volume of one or more ternary agents used in the present method is typically in the range of about 0.1 M to about 10 M.

One or more polymers may be used in accordance with the present invention. Suitable polymers for use in the method of the present invention include for example but are not limited to polyolefins, polyesters, polyanhydrides, polyorthoesters, polyurethanes, polyethylene and its derivatives, all acrylate-based polymers including poly(acrylic acid), poly(methyl methacrylate) and poly(2-hydroxyethyl methacrylate), poly(N-vinylpyrrolidone) and polyethylenimine. Preferred polymers include polyurethanes and polysaccharides because the same allow optimal particle forming properties to be included in the material selection. The volume of one or more polymers used in the present method is typically in the range of about 0.01 percent w/v solvent/non-solvent system to about 1.0 percent w/v solvent/non-solvent system.

One or more matrices may be used in accordance with the present invention. Suitable matrices for use in the method of the present invention include for example but are not limited to trehalose, dextrose, triethanolamine, tetraethyl orthosilicate and calcium carbonate. Preferred matrices include trehalose, dextrose and triethanolamine because of their lyoprotectant and ionic interaction properties. The volume of one or more matrices used in the present method is typically in the range of about 0.01 percent w/v solvent/non-solvent system to about 1.0 percent w/v solvent/non-solvent system.

One or more solvents having temperature dependent solubility may be used in accordance with the present invention. Suitable solvents having temperature dependent solubility for use in the method of the present invention include for example but are not limited to acetone, acetonitrile, ethanol, isopropyl alcohol, dimethyl sulfoxide, dimethyl formamide, tetrahydrofuran and dioxane. Preferred solvents having temperature dependent solubility include acetone and acetonitrile because of their relatively strong solvating power. The volume of one or more solvents having temperature dependent solubility used in the present method is typically in the range of about 5.0 percent v/v of the solvent/non-solvent system to about 50 percent v/v of the solvent/non-solvent system.

One or more surfactants may be used in accordance with the present invention. Suitable surfactants for use in the method of the present invention include for example but are not limited to poly(N-vinylpyrrolidone), poly(ethylene oxide)/poly(propylene oxide) triblock copolymers, Tweens, Sorbitans and triacyl glycerols. Preferred surfactants include poly(ethylene oxide)/poly(propylene oxide) triblock copolymers because the broad range of polymers allows for the selection of an optimal stabilizing agent. The volume of one or more surfactants used in the present method is typically in the range of about 0.1 percent w/v of the solvent/non-solvent system to about 5.0 percent w/v of the solvent/non-solvent system.

One or more monomers, macromonomers or a combination thereof may be used in accordance with the present invention. Examples of such include for example but are not limited to poly(ethylene glycol) diamethacrylate, methylene bisacrylamide, 2-hydroxyethyl methacrylate, methyl methacrylate, acrylic acid, methacrylic acid 2-ethylhexyl methacrylate, 3-methacryloyloxypropyldiphenylmethylsilane, 3-methacryloyloxypropyltris(trimethylsiloxy)silane, 2-phenyoxyethyl methacrylate, poly(proprionic acid) and copolymers containing poly(proprionic acid), polycaprolactone dimethacrylate and other methacrylate, glycidyl and cyanoacrylate end-capped macromonomers.

One or more initiators may be used in accordance with the present invention. Suitable initiators include for example but are not limited to free radical thermal polymerization initiators such as azobisisobutyronitrile, acetyl peroxide, lauroyl peroxide, decanoyl peroxide, stearoyl peroxide, benzoyl peroxide, tert-butyl peroxypivalate, peroxydicarbonate, and the like. Suitable initiators also include ultraviolet light initiators such as for example but not limited to benzoin methyl ether, benzoin ethyl ether, Darocur™ 1173, 1164, 2273, 1116, 2959, 3331 (Ciba-Geigy, Basel, Switzerland) and Irgacur™ 651 and 184 (Ciba-Geigy).

One or more agent solvents may be used in accordance with the present invention. Suitable agent solvents for use in the method of the present invention include polar charged, polar uncharged, polar, charged or neutral solvents, such as for example but not limited to chloroform, carbon tetrachloride, 1,2-dichloroethane, dichloromethane, ethyl acetate and toluene. The preferred agent solvent is ethyl acetate because of its solubility in many non-solvents. The volume of one or more agent solvents used in the present method is typically in the range of about 0.01 percent of the solvent/non-solvent system to about 10.0 percent of the solvent/non-solvent system.

One or more therapeutic agents may be used in accordance with the present invention. Suitable therapeutic agents for use in the method of the present invention include for example but are not limited to beta-blockers, anti-glaucoma agents such as for example but not limited to the beta blockers timolol maleate, betaxolol and metipranolol, miotics such as for example but not limited to pilocarpine, acetylcholine chloride, isofluorophate, demacarium bromide, echothiophateiodide, phospholine iodide, carbachol and physostigimine, epinephrine and salts such as for example but not limited to dipivefrin hydrochloride, dichlorphenamide, acetazolamide and methazolamide, anti-cataract and anti-diabetic retinopathy agents such as for example but not limited to the aldose reductase inhibitors tolrestat, lisinopril, enalapril and statil, thiol cross-linking agents, anticancer agents such as for example but not limited to retinoic acid, methotrexate, adriamycin, bleomycin, triamcinoline, mitomycin, cisplatinum, vincristine, vinblastine, actinomycin-D, ara-c, bisantrene, activated cytoxan, melphalan, mithramycin, procarbazine and tamoxifen, immune modulators, anti-clotting agents such as for example but not limited to tissue plasminogen activator, urokinase and streptokinase, anti-tissue damage agents such as for example but not limited to superoxide dismutase, proteins and nucleic acids such as for example but not limited to mono- and polyclonal antibodies, enzymes, protein hormones and genes, gene fragments and plasmids, steroids, particularly anti-inflammatory or anti-fibrous agents such as for example but not limited to loteprednol, etabonate, cortisone, hydrocortisone, prednisolone, prednisome, dexamethasone, progesterone-like compounds, medrysone (HMS) and fluorometholone, non-steroidal anti-inflammatory agents such as for example but not limited to ketrolac tromethamine, dichlofenac sodium and suprofen, antibiotics such as for example but not limited to loridine (cephaloridine), chloramphenicol, clindamycin, amikacin, tobramycin, methicillin, lincomycin, oxycillin, penicillin, amphotericin B, polymyxin B, cephalosporin family, ampicillin, bacitracin, carbenicillin, cepholothin, colistin, erythromycin, streptomycin, neomycin, sulfacetamide, vancomycin, silver nitrate, sulfisoxazole diolamine and tetracycline, other antipathogens including anti-viral agents such as for example but not limited to idoxuridine, trifluorouridine, vidarabine (adenine arabinoside), acyclovir (acycloguanosine), pyrimethamine, trisulfapyrimidine-2, clindamycin, nystatin, flucytosine, natamycin, and miconazole, piperazine derivatives such as for example but not limited to diethylcarbamazine, and cycloplegic and mydriatic agents such as for example but not limited to atropine, cyclogel, scopolamine, homatropine and mydriacyl.

Other therapeutically active agents or drugs include anticholinergics, anticoagulants, antifibrinolytics, antihistamines, antimalarials, antitoxins, chelating agents, hormones, immunosuppressives, thrombolytics, vitamins, salts, desensitizers, prostaglandins, amino acids, metabolites and antiallergenics.

Therapeutically active agents or drugs of particular interest include hydrocortisone (5-20 mcg/l as plasma level), gentamycin (6-10 mcg/ml in serum), 5-fluorouracil (~30 mg/kg body weight in serum), sorbinil, interleukin-2, phakan-a (a component of glutathione), thioloa-thiopronin, bendazac, acetylsalicylic acid, trifluorothymidine, interferon ($\alpha$, $\beta$ and $\gamma$), immune modulators such as for example but not limited to lymphokines and monokines and growth factors. Preferred therapeutic agents include proteins and nucleic acids because this method is relatively mild allowing high retention of biomolecule activity. The volume of one or more therapeutic agents used in the present method is typically in the range of about 1.0 percent to about 45 percent.

The present method is useful for the production of nanoparticles and microparticles through the use of ternary agent concentration and temperature alteration induced immiscibility as is described in more detail below. A solution of one or more non-solvents, one or more ternary agents, and one or more surfactants are prepared at a starting temperature. One or more polymers, one or more matrices or combinations of one or more polymers and one or more matrices are dissolved in a selected solvent or solvent system. One or more desired therapeutically active agents are dissolved in a selected agent solvent or agent solvent system. Either the polymer and/or matrix solution is mixed with the therapeutically active agent solution before addition to the non-solvent solution, or the two are added separately to the non-solvent solution. The temperature of the solution of non-solvent(s), ternary agent (s), surfactant(s), polymer and/or matrix solution and therapeutically active agent solution is either increased or decreased to reduce the solubility of the solvents in the non-solvent solution. Changes in temperature may be performed rapidly or slowly, continuously or stepwise, or linearly or non-linearly. With the associated change in temperature, solvent(s) form emulsions with the non-solvent solution. Emulsified solvents may consist of elements of the solvent system for polymer or matrix or combinations thereof, and/or elements of the solvent system for the active therapeutic agent (s). Emulsified solvent being a better solvent for polymer or matrix or a combination thereof or for one or more active agents than the solvent and non-solvent system, therapeutically active or inactive agents preferentially partition into the better solvent.

Emulsification may be controlled to preferentially force one solvent out of the non-solvent solution to effect formation of a core of material or regions with different relative amounts materials or densities of a single material, therapeutically active or inactive. Temperature alteration profile may be controlled to produce a core of material or regions with different relative amounts materials or densities of a single material, therapeutically active or inactive. Because all emulsified droplets form from the same solution and grow under similar conditions, a narrow particle size distribution can be achieved for particles from about 1 nm to about 1 mm in size.

Following polymerization, solvent is removal by alteration of pressure or vapor phase composition. Solvent removal may accompany different stages of nanoparticle or microparticle formation. Removal may be controlled to remove selected solvent or solvents or part of selected solvent or solvents. The timing of temperature change and solvent removal is controlled to produce particles in the size range from 0.10 nm to 1 mm. In the final phase, solvent removal is extensive enough to produce hardened polymeric or matrix particles.

The method of the present invention is described in still greater detail in the following example.

EXAMPLE 1

Poly(dimethyl siloxane) Nanospheres and Microspheres Prepared Using Water, Acetone and Sodium Chloride System In a specific embodiment of the method of the present invention, the non-solvent is water, the ternary agent is sodium chloride, the surfactant is a poly(ethylene oxide)-poly (propylene oxide)-poly(ethylene oxide) triblock copolymer commercially available under the trade name Pluronic F127™ (BASF Wyandotte Corp.). Tetrahydrofuran (THF) is used as the polymer and therapeutic agent solvent. The monomer is a bismethacrylate end-capped poly(dimethyl siloxane) ($M_2D_{100}$) ($M_2$= bismethacrylate; $D_{100}$= poly(dimethyl siloxane) backbone). Evaluating the effect of temperature change on THF solubility in the non-solvent solution, it was determined that THF possesses a solubility maximum in a solution of sodium chloride in water at 22° C. Furthermore, it was determined that the change in solubility over the temperature range of 25° C. to 50° C. the change in the solubility was inversely proportional to the salt concentration from 5 to 1 M. A useable change in the solubility was for a 30 percent solution of acetone in 1 M sodium chloride solution in water. At 10° C., 30 percent THF was completely soluble in the non-solvent salt solutions, but the volume occupied by the THF phase was approximately 10.0 percent of the total volume when the temperature was increased to 45° C. After mixing the non-solvent solution, 1 M sodium chloride and 1 percent Pluronic F127™ in water, 30 percent THF containing 0.27% $M_2D_{100}$ and 0.35% Darocur™ initiator (Ciba-Geigy) was added. The combination of the two solutions was cooled to 10° C. After reaching the temperature required to fully dissolve the solvent in the non-solvent solution, the entire volume was transferred to a vacuum flask at 45° C. and stirred. When it was confirmed that the temperature of the solvent and non-solvent solution was 45° C., the resulting phase-separated suspension was irradiated with ultraviolet light for one hour to initiate and propagate the reaction of the methacrylate end groups. Following the polymerization reaction, vacuum was drawn to remove the THF. The resulting hardened particles were collected by filtration through a 100 nm filter, rinsed and dried. Analysis using dynamic light scattering, scanning electron microscopy, and atomic force microscopy confirmed that particles were created and that the particle size was controlled, repeatable and monodisperse.

The greater the volume of solvent emulsified in the non-solvent, the smaller the particle size. Assuming emulsion droplets originate from a continuous solution, all droplets must begin forming at the same size. For a constant amount of polymer soluble in the solvent, the more emulsion droplets that form, the smaller the mass of polymer in each droplet. After droplets are hardened, the smaller mass dissolved in the droplet results in a smaller final particle. Varying the amount of polymer dissolved in the solvent and the amount of the temperature change varies the amount of polymer that dissolves in the emulsion droplet and the number of emulsion droplets formed, respectively. Additionally, starting with a different salt concentration would alter the amount of solvent that emulsifies on temperature alteration and ultimately particle size. The elements of this process provide excellent control of the formation of particles in the size range from about 0.10 nm to less than about 1 mm.

The uniqueness of this method of the present invention is that it differs from the prior art body of knowledge in that the solvent and non-solvent are miscible, a ternary agent is introduced in to the non-solvent to make the solvent and non-solvent immiscible, the concentration of the ternary agent remains constant, the ternary agent concentration makes the solvent for the polymer or matrix insoluble, not only the polymer or matrix, temperature is used to grow particles to the desired size, a single preparation method can be used to create particles from about 0.10 nm to less than about 1 mm. An advantage of this method as compared to other particle polymerization methods is the ability to produce spheres of materials that are not inherently soluble in one another, but soluble in a common solvent. Such a property is required for loading particles with therapeutically active agents or adjusting mechanical properties of particles consisting of several polymers.

Drug delivery agents produced in accordance with the present method may be used in all cases contacting bodily fluids. Such uses include for example but not limited to topical applications, such as for example but not limited to lotions, gels or suspensions, especially for external delivery to the eye; enteric administration such as for example but not limited to direct ingestion or indirect ingestion via inhalation or naso-lacrimal duct; parenteral administration such as for example but not limited to hypodermic injection into the tissues of the body including for example but not limited to vitreous humor, aqueous humor, cornea, sclera, retina and choroids; and inhalation into the lungs.

While the invention has been described in conjunction with specific examples thereof, this is illustrative only. Accordingly, many alternatives, modifications, and variations will be apparent to those skilled in the art in the light of the foregoing description and it is, therefore, intended to embrace all such alternatives, modifications, and variations as to fall within the spirit and scope of the appended claims.

We claim:

1. A method for the production of polymer-containing particles comprising:
   combining (a) a non-solvent; (b) a ternary agent; (c) a surfactant; (d) a monomer, macromonomer, or a combination thereof; and (e) an initiator to produce a non-solvent solution;
   combining a solvent that is miscible with said non-solvent, and a polymer that is soluble in said solvent to produce a solvent solution; and
   combining said non-solvent solution and said solvent solution to produce polymer-containing particles as a result of a phase separation between a non-solvent phase and a solvent phase induced by an amount of said ternary agent.

2. A method for the production of polymer-containing particles, the method comprising:
   combining: (a) water; (b) sodium chloride; (c) sodium bromide; (d) poly(ethylene oxide)/poly(propylene oxide) triblock copolymers; one or more monomers, macromonomers or a combination thereof; and one or more initiators to produce a non-solvent solution;
   combining: (a) acetone; (b) acetonitrile; and one or more (c) (i) polysaccharide and polyurethane polymers, or (ii) trehalose, dextrose and triethanolamine, or (iii) a combination thereof to produce a solvent solution; and
   combining said non-solvent solution with said solvent solution to produce polymerized particles ranging in size from about 0.10 nm to about 1 mm.

3. The method of claim 1 or 2 wherein said monomer or macromonomer is selected from the group consisting of poly (ethylene glycol) diamethacrylate, methylene bisacrylamide, 2-hydroxyethyl methacrylate, methyl methacrylate, acrylic acid, methacrylic acid2-ethylhexyl methacrylate, 3-methacryloyloxypropyldiphenylmethylsilane, 3-methacryloyloxypropyltris (trimethylsiloxy)silane, 2-phenyoxyethyl methacrylate, poly(proprionic acid) and copolymers containing poly(proprionic acid), polycaprolactone dimethacrylate and other methacrylate, glycidyl and cyanoacrylate end-capped macromonomers.

4. The method of claim 1 or 2 wherein said initiator is selected from the group consisting of azobis-isobutyronitrile, acetyl peroxide, lauroyl peroxide, decanoyl peroxide, stearoyl peroxide, benzoyl peroxide, tert-butyl peroxypivalate, peroxydicarbonate, benzoin methyl ether, benzoin ethyl ether.

5. The method of claim 1 or 2 wherein said initiator is selected from the group consisting of free radical thermal polymerization initiators, ultraviolet light initiators, and blue light initiators.

6. The method of claim 1 or 2 wherein size of said polymer-containing particles is controlled through temperature variation.

7. The method of claim 1 or 2 wherein size of said polymer-containing particles are about 1 mm to about 0.10 nm in size.

8. The method of claim 1 or 2 wherein size of said polymer-containing particles are about 400 nm to about 0.10 nm in size.

9. The method of claim 1 or 2 wherein size of said polymer-containing particles are about 350 nm to about 0.50 nm in size.

10. The method of claim 1 or 2 wherein said solvent is selected from the group consisting of acetone, acetonitrile, ethanol, isopropyl alcohol, dimethyl sulfoxide, dimethyl formamide, tetrahydrofuran and dioxane.

11. The method of claim 1 wherein solvent is acetone, acetonitrile or a combination thereof.

12. The method of claim 1 wherein said non-solvent is selected from the group consisting of water, alcohols, ethers, amine-containing solvents, carboxyl-containing solvents and organic solvents.

13. The method of claim 1 wherein non-solvent is water, methanol, ethanol or a combination thereof.

14. The method of claim 1 wherein said ternary agent is selected from the group consisting of ammonium azide, ammonium bisulfite, barium acetate hydrate, barium hypophosphate, cadmium chloride, calcium acetate dihydrate, calcium chromate, calcium ethyl methyl acetate, cobalt perchiorate, iron perchiorate hexahydrate, lead chlorate hydrate, lithium hydroxide monohydrate, lithium sulfate, lithium sulfite monohydrate, potassium carbonate, potassium chloride, sodium selenate, sodium stannate (hydroxo), strontium acetate and yttrium chloride.

15. The method of claim 1 wherein said ternary agent is sodium chloride, sodium bromide or a combination thereof.

16. The method of claim 1 wherein said polymer is selected from the group consisting of polyesters, polyanhydrides, polyorthoesters, polyurethanes, polyethylene and its derivatives, all acrylate-based polymers including poly(acrylic acid), poly(methyl methacrylate) and poly(2-hydroxyethyl methacrylate), poly(N-vinylpyrrolidone) and polyethylenimine.

17. The method of claim 1 wherein said solvent solution further comprising a material selected from the group consisting of trehalose, dextrose, triethanolamine, and calcium carbonate.

18. The method of claim 1 wherein said surfactant is selected from the group consisting of poly(N-vinylpyrrolidone), poly(ethylene oxide)/poly(propylene oxide) triblock copolymers, Tweens, Sorbitans and triacyl glycerols.

19. The method of claim 1 or 2 wherein said polymer-containing particles are useful as drug delivery agents.

20. The method of claim 1 or 2 wherein said polymer-containing particles are useful as ophthalmic drug delivery agents.

* * * * *